United States Patent [19]
Stanton

[11] Patent Number: 5,428,277
[45] Date of Patent: Jun. 27, 1995

[54] AUTOMATED CONTROLLED WINDSCREEN WIPING

[75] Inventor: Peter R. Stanton, North Manly, Australia

[73] Assignee: Introlab Pty. Limited, North Manly, Australia

[21] Appl. No.: 133,245

[22] Filed: Oct. 8, 1993

Related U.S. Application Data

[63] Continuation-in-part of Ser. No. 836,012, Feb. 26, 1992, abandoned.

[30] Foreign Application Priority Data

Aug. 28, 1989 [AU] Australia ................................ PJ5987
Aug. 28, 1989 [AU] Australia ................................ PJ5988

[51] Int. Cl.⁶ .......................... B60S 1/08; G01N 21/47
[52] U.S. Cl. .................... 318/444; 318/480; 318/483; 318/DIG. 2
[58] Field of Search ............... 318/443, 444, 480, 483, 318/DIG. 2; 388/907.5, 933; 15/250.12, 250.13, 250.17

[56] References Cited

U.S. PATENT DOCUMENTS

| | | |
|---|---|---|
| 3,604,997 | 9/1971 | Kirchner et al. |
| 4,499,410 | 2/1985 | Iacoponi et al. |
| 4,527,105 | 7/1985 | Shiraishi |
| 4,595,866 | 6/1986 | Fukatsu et al. .................. 318/444 |
| 4,620,141 | 10/1986 | McCumber et al. ............... 318/483 |
| 4,916,374 | 4/1990 | Schierbeek et al. .............. 318/483 |

FOREIGN PATENT DOCUMENTS

| | | |
|---|---|---|
| WO91/03393 | 3/1991 | Australia . |
| 2504799 | 6/1976 | Germany . |
| 3244767 | 6/1984 | Germany . |

Primary Examiner—Bentsu Ro
Attorney, Agent, or Firm—Nikaido, Marmelstein, Murray & Oram

[57] ABSTRACT

A system for automatically controlling the wiping of automotive windscreens is disclosed. The wiping is conducted at a rate corresponding to the amount of water determined to be on the windscreen at each wiping cycle.

24 Claims, 4 Drawing Sheets

AUTOMATED CONTROLLED WINDSCREEN WIPING

CROSS REFERENCE TO RELATED APPLICATIONS

This application is a continuation-in-part of international application number PCT/AU92/00156, filed Apr. 9, 1992, and designating the United States of America, and a continuation-in-part of U.S. application Ser. No. 07/836,012, filed Feb. 26, 1992, now abandoned, which was a U.S. national phase entry application of international application number PCT/AU90/00380, filed Aug. 28, 1990.

This invention relates to a system for automatically controlling the wiping of automotive windscreens at a rate corresponding to the amount of water determined to be on the windscreen at each wiping cycle.

BACKGROUND

In Australian patent 546327, a detector mounted externally of the vehicle continuously monitors rain to provide a value for the amount of rain fallen since the completion of the last wipe of the windscreen wiper blade. Once that rain total reaches some predetermined level the wiper blade is again actuated. Such is typical of prior art automatic windscreen wiper controls which integrate detected actual rainfall signals in order to determine the rate or frequency of windscreen wiper operation.

However, such systems are in general deficient, at least in regard to the fact that the windscreen needs to be wiped not only in consideration of rainfall, but also in consideration of other water sources such as spray from nearby cars.

It is known to control windscreen wiper systems in response to measurements taken by a moisture sensing device. Typically in the prior art the moisture sensing device attempts to measure the rate of precipitation and the control attempts to initiate a wiping action once some predetermined amount of precipitation has occurred. While many such systems have been postulated, very few have apparently come into existence and those generally suffer erratic operation under at least certain conditions.

SUMMARY OF THE INVENTION

The present invention is an automated controlled windscreen wiping method and apparatus which senses the amount of light reflected from a surface of the windscreen and uses variations of detected light to determine the amount of moisture on the surface, and controls a windscreen wiper to sweep at a rate that varies with the determined amount of moisture in each action of a wiper blade. A specific feature is that the amount of moisture is determined by measuring the signal variation caused by a wave or wall of water that precedes the wiper blade as it passes the area of the sensor.

It is an object of the present invention to provide a method of controlling a wiper system, once it has been actuated, so as to automatically control the rate of wiping of the windscreen in an effective manner.

Accordingly, in one broad form, the present invention can be said to provide a control means for a windscreen wiping system having variable wiping rates, wherein the control means sets a future wiping rate dependent upon a present wiping rate and a quantitative measure of the amount of moisture swept by the wiper blade across the windscreen during a current wiper action, the control means having input means for receiving a signal corresponding to a moisture value indicative of said quantitative measure of moisture from a moisture sensor, output means providing a control signal for a wiper motor control which defines a future wiping rate according to a current wiping rate and the moisture value, processing means for determining the control signal by applying a current wiping rate value and the moisture value to pre-programmed data, wherein said pre-programmed data provides a control signal value predetermined to be appropriate for current absolute moisture accumulation rates and indexed by the current wiping rate value and the moisture value.

Preferably the quantitative measure of moisture level is provided by a sensor indicating the amount of water wiped from the windscreen during at least a portion of a single wiping action of the wiper system. Most preferably the sensor indicates the width of a water wave formed by a wiper action at a point within and proximate an end edge of an area swept by the wiper.

In one form the method of control includes determining a current value of the wiping rate and a moisture value corresponding to an absolute moisture level determined during a preselected wiper action, and setting a future wiping rate according to a predetermined table based on the current value and the moisture value.

In another form the method of control employs a system in which the current wiping rate is set by a speed controller which responds to speed up and slow down signals by respectively increasing or decreasing the wiping rate, the method including determining a relative moisture value which is the inverse of the moisture present on the screen and comparing this value to a value representing a predetermined moisture level, determining whether the measured relative moisture value is equal to, greater than or less than the predetermined moisture level and signalling the controller to respectively remain constant, slow down, or speed up the wiping rate. Preferably the relative moisture value further includes a discrepancy measure and any speed up or speed down signal includes a quantitative portion based on the discrepancy measure and determining the proportional change in wiping rate.

Generally, the invention relies on measurements of precipitation rate by averaging out the precipitation accumulated during a preselected wiper action, conveniently being the current (or last) sweep of the wiper blade, and by using that information in conjunction with information of the wiping rate used for that wiping action to determine the next wiping rate. Two basic criteria can be used in finally selecting a future (or next) wiping rate. Fundamentally there is an ideal amount of moisture to be swept from the screen each wiper action, this amount relates to the level of moisture accumulated on the screen which is sufficient to hinder clear vision. For a given wiper action, if the detected moisture level is undesirably greater or less than the ideal level, the next wiping rate to be used can be set respectively faster or slower than the present rate. Also by measuring the amount of moisture swept from the screen in a single sweep, i.e. the moisture averaged over a single wiper action, and dividing by the time lapsed since the last sweep (the current time delay), the actual rate of moisture accumulation, or the absolute moisture accumulation rate as an average over that period is calculated, and a predetermined wiper rate corresponding to the calculated absolute accumulation rate can be set.

By averaging the moisture accumulation of the period of a wiping action, and by taking direct account of the current wiping rate, accurate and consistent wiper action can be obtained automatically.

Preferably the setting of the wiping rate is effected each wiping sweep of the wiping system.

BEST MODE OF CARRYING OUT THE INVENTION

Figure 1:
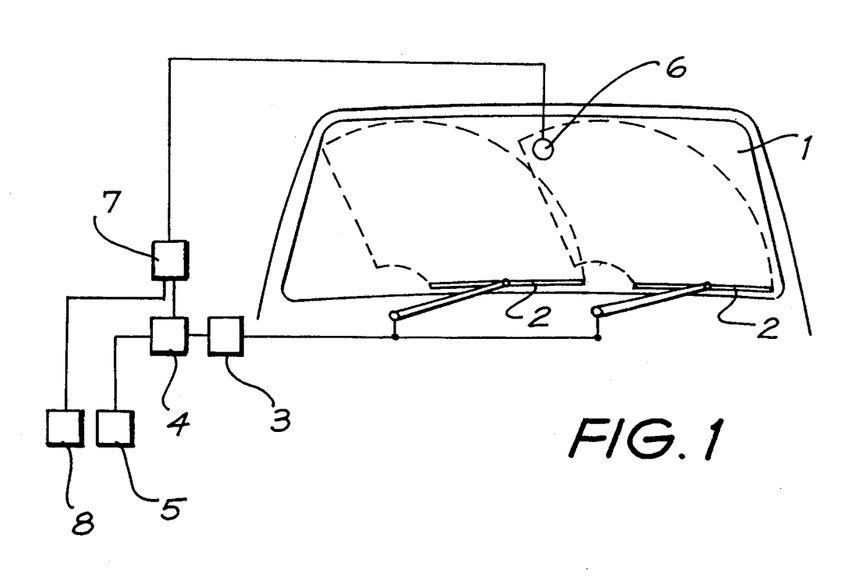
FIG. 1 shows a schematic arrangement of a road vehicle windscreen wiping system incorporating the invention.

FIG. 1 schematically shows the main components of a windscreen wiping system for a vehicle in accordance with the invention. The vehicle normally includes a windscreen 1, a pair of wiper blades 2, a wiper motor 3, and a motor controller 4 which is normally switched on and off by a manual control 5 and controlled to provide fast, slow, intermittent (fixed or variable) and off wiper blade speeds. When fitted with equipment according to the invention it additionally includes a moisture sensor 6; an automatic wiper control 7, and a momentary starting switch 8.

The moisture sensor 6 operates by directing a beam of light energy toward the surface of the windscreen and detecting the amount of light energy reflected from the windscreen. Preferably the light is in the infra-red range emitted by a light emitting diode; however, an infra-red laser beam may also be used.

Figure 2A:
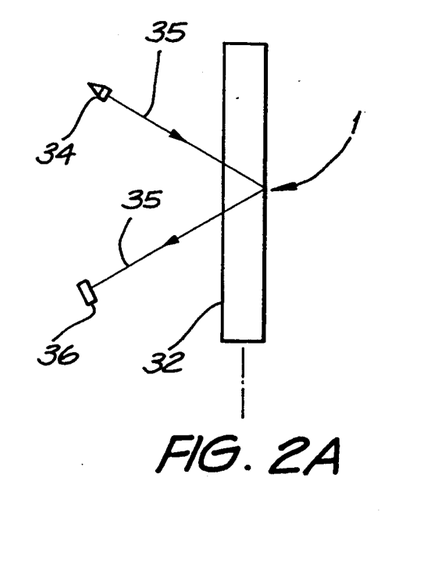
FIGS. 2A and 2B schematically show an exemplary embodiment of means for detecting the moisture state on the outside of a windscreen.
Figure 2B:
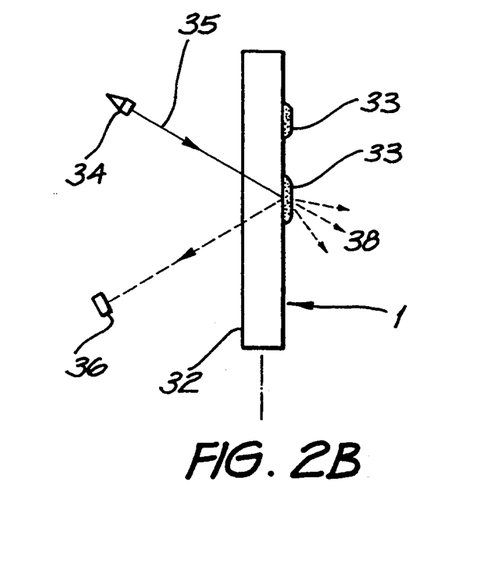

As shown in FIGS. 2A and 2B an infra-red (IR) light beam 35 is provided by diode (LED) 34 and directed generally along a path toward windscreen 1. The angle of incidence is selected such that at least a high proportion of the beam 35 travels through the material of windscreen 1 to be internally reflected off the outside surface of the windscreen, when the outside surface is dry, and to continue along a path to IR light detector 36.

The presence of water, such as water drops 33, on the outside surface at the point of incidence of beam 35, will result in a substantial portion of diffused light 38 being lost from the beam 35. Thus, with water on the outside of the wind screen 1, the amount of IR light detected at detector 36 is diminished allowing detector 36 to provide a signal to an electronic logic circuit or other electronic device, which signal is indicative of the presence of water on the windscreen.

It will be clear that the operation of the device depends upon the presence of water altering the refractive index at the screen/air exterior interface. As such, operation of the device is not restricted to detecting water droplets, but will also detect for example ice. Thus, throughout this specification, it should be clear that the term "wet" defines the presence of water in any state and the term "dry" defines the absence of water in any state.

An automatic wiper control 7 as described hereafter is connected to the moisture sensor 6 as shown in FIG. 1 and upon receipt of a manual start signal or a signal indicating water on the windscreen 1, initiates a first wiping action of the windscreen wiper blades. The moving wiper blade produces a wall or wave of water along its leading edge which is characteristically proportional to the amount of water that was on the windscreen at the time of the wiper blade sweep. As this wall of water passes the point of incidence of the beam 35 in moisture sensor 6, the light detector 36 receives a varying amount of reflected light beam 35 and thus produces a variation in signal strength which is directly related to the amount of moisture that was wiped by the wiper blade from the screen. This signal indicating the amount of moisture on the screen is then processed and used to control the next sweep of the blade. Such control of the blade can be related to the blade sweep speed, or a lag time between the last and next sweep of the blade.

When the windscreen becomes dry the reflected beam 35 reaching the detector 36 become constant and the wipers are switched off.

Figure 3A:
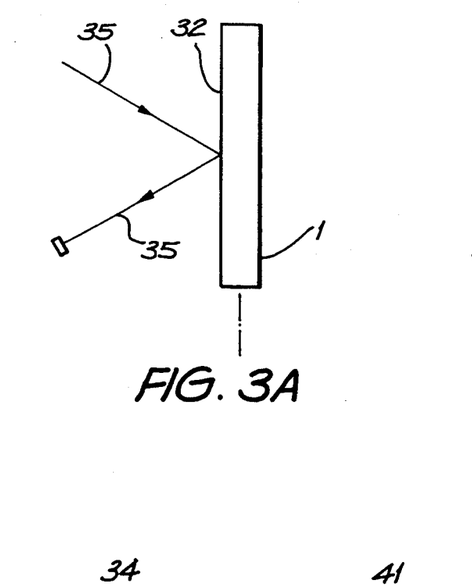
FIGS. 3A and 3B schematically show an exemplary embodiment of means for detecting the moisture state on the inside of a windscreen.
Figure 3B:
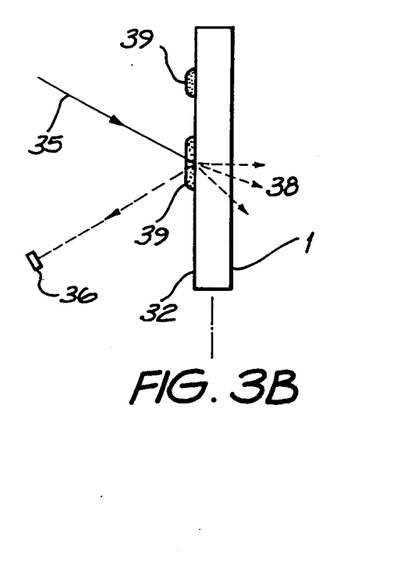

In FIGS. 3A and 3B the infra red beam 35 is directed at the windscreen at an angle of incidence so as to create substantial external reflection from the inside surface 32 of the windscreen. Here, the presence of misting, creating moisture condensation 39 on the inside 32, is measured by detector 36, where the amount of light detected is diminished due to light dispersion 38, in a manner similar to that described before with reference to FIGS. 2A and 2B. In this case detector 36 is connected via circuitry to demisting equipment of the vehicle.

Figures 4A, 4B:
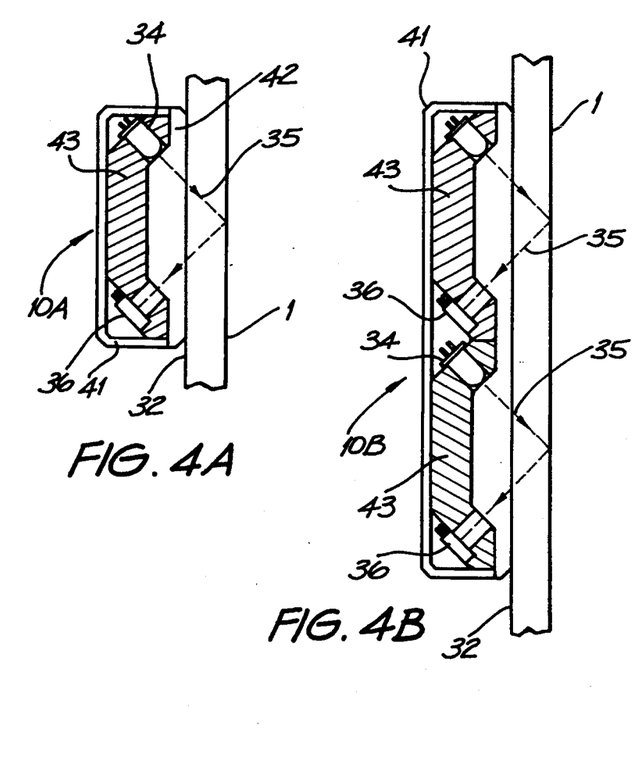
FIGS. 4A and 4B are sectional views of a light reflection detector means.

FIGS. 4A and 4B show in plan similar integral light sensor assemblies 10A and 10B which embody in a particular form the devices shown in FIGS. 2A and 2B and described above.

The light sensor assembly 10A includes a front window 42 which is transparent to infra red light and which is adhered to, and optically matched with, the inside surface 32 of the windscreen 1. In a rear face of the window 42 is an array of three infra-red LEDs 34 to produce beams 35 angled at the windscreen. The light beams 35 strike the outside surface at the desired angle of incidence to be reflected back into the window 42 and impinge on a matching set of three diode light detectors 36.

Respective co-operative LED 34 and detector 36 pairs are housed in a sensor module 43, three modules 43 being located side by side within a case enclosure 41, creating a pattern of three closely spaced illumination points which ensure correct operation even with defective wiper blades. The device is well adaptable to rear windscreens of cars which include wipers.

Figure 4C:
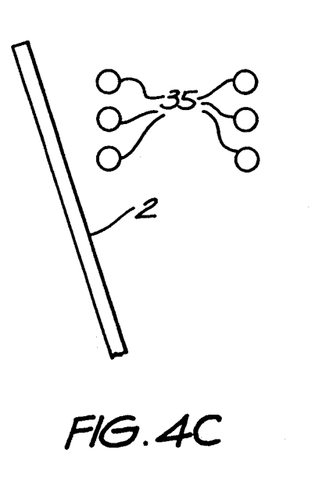
FIG. 4C is a schematic representation of a light beam pattern on a windscreen.

The light assembly 10B comprises six of the modules 43 arranged in two rows of three. The pattern of illumination created by assembly 10B is shown in FIG. 4C and its broad area allows connected electronics to override deleterious effects affecting the signal from a single module such as debris, e.g. impacted insects, as well as water streaks caused by faulty wiper blades. The assembly 10A or 10B is fixed with the front face of the window 42 flush against the inner windscreen surface 32 to form a detection region at any convenient point aligned with a portion of the outside surface that is wiped by a wiper blade 2. In a typical road vehicle front windscreen the position of the detection region can often be between the windscreen and the interior rear vision mirror.

The windscreen may be any screen which is to be kept clear of rain or similar by some controllable cleaning mechanism such as, but not necessarily, a pendulous wiper. It does have particular use in road vehicles, boats and aeroplanes.

When the sensor 6 and the automatic wiper control 7 are switched on via a momentary switch 8, windscreen wiper operation commences and the automatic wiper control 7 adjusts the rate of wiping by the wiper blades 2 in accordance with the amount of water detected on the windscreen.

Depending on the amount of detected moisture, the manner of regulating the rate of wiping may be accomplished selectively by altering the actual speed of the motor 3, or by adjusting a time delay between the end of one wiping action and the beginning of the next wiping action. In either case, the rate of wiping is continually updated after each wiping action.

Figure 5:
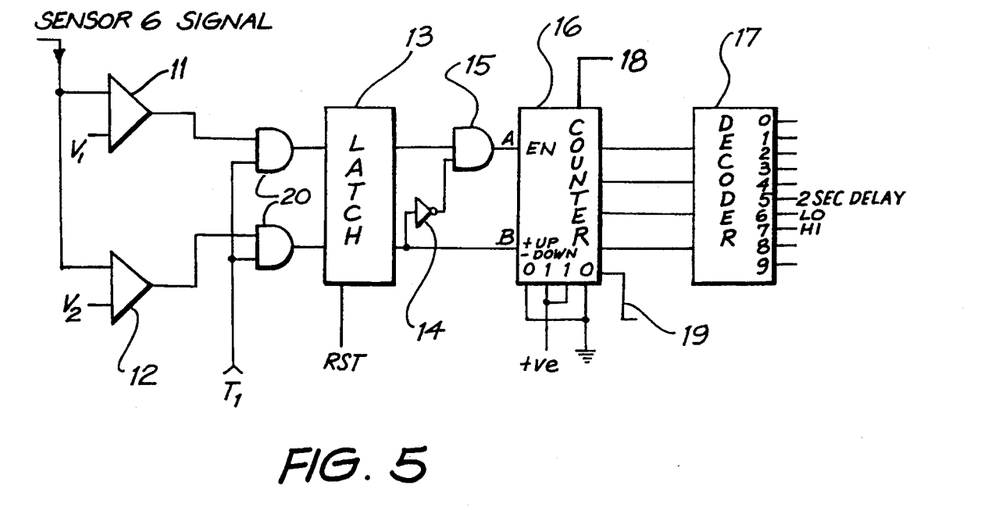
FIG. 5 is a schematic circuit diagram of a control system that may be used in one embodiment of the invention.

One embodiment of an automatic wiper control 7 is shown, by schematic circuit diagram, in FIG. 5. The control 7 receives a signal from the moisture sensor 6, the signal goes to a pair of comparators 11 and 12. The signal derived from the sensor 6 is a variable voltage dependent upon the measured amount of water swept by the blade 2 during the current wiping action. The comparators 11 and 12 are also connected to preselected respective reference voltages $V_1$ and $V_2$, $V_1$ being a higher voltage than $V_2$. This enables the signal from sensor 6 corresponding to the inverse of the measured moisture at a specified time $T_1$ to be categorized into one of three areas i.e. greater than $V_1$, less than $V_1$ but greater than $V_2$, or less than $V_2$. These categories relate to little or no moisture, a small amount of water swept by blade 2, or a large amount of water swept by blade 2, respectively. The principle of operation is to adjust the wiping rate automatically, so that the signal level from sensor 6 is kept within the second category as previously described. Specifically, by increasing the wiping rate, the amount of water swept by blade 2 each wiping cycle is reduced, and conversely a reduction in the wiping rate will increase the amount of water swept by blade 2 each cycle. As stated above, the signal voltage from sensor 6 is inversely proportional to the amount of water being swept by blade 2, i.e. a large sensor voltage represents a small amount of water and visa-versa. This inverse relationship results from a greater amount of light being reflected from a dry window to light detectors 36, while moisture produces light dispersion that lowers the signal outputs from detectors 36.

Outputs from the comparators 11 and 12 lead through two AND gates 20, and thence into a latch 13. From the latch 13 signals derived from comparator 12 lead to pin B of an up/down counter 16. Signals derived from the comparator 11 lead through an AND gate 15 into pin A of the counter 16. The counter 16 is also connected to a clock 18 providing timing pulses every wiping cycle. Also, a load input signal 19 enables an initial count, binary six (0110), causing low speed to be selected on decoder 17 when the wiper operation commences.

The AND gate 15 also receives an inverted signal as derived from comparator 12 via the inverter 14.

In operation the comparators 11 and 12 will provide respective negative and positive outputs if an amount greater than a predetermined amount of water is swept by a wiping action causing a positive input at pin B of the counter 16, and at the next clock pulse from clock 18 the counter 6 will count up. After such an up count the decoder 17 will output negatively through pin 6 and positively through pin 7 to motor controller 4, changing the wiper rate from low to high speed.

Respective positive and negative outputs from comparators 11 and 12, as a result of the set predetermined amount of water being swept by a wiping action, will cause a positive input at pin A to inhibit the clock count and therefore prevent either up or down counts by the counter 16. Thus, in this condition, the wiper remains at whatever wiper rate it is set.

When both comparators 11 and 12 give negative outputs as a result of less than the predetermined amount of water being swept by a wiping action, then both inputs A and B of the up/down counter 16 will be negative, the clock count will continue and the counter 16 will count down on the next clock pulse. The decoder 17 will then output positively at pin 6 switching the wiper rate back to low speed. If both comparators 11 and 12 again output negative the next down count from counter 16 will result in a positive output at pin 5 of decoder 17 and the wiping system will go into intermittent mode with, for example, a two second delay between wiping cycles.

Where variable intermittent time delays are available the decoder 17 can be correspondingly programmed so as to provide counting up and down through the entire available wiping rates. Clearly, if counting down continues the system will end up on the slowest rate or completely stopped.

While the system shown in FIG. 5 provides one hardware design for implementing an up/down counter based control system, other hardware solutions will clearly be available, including microprocessor based systems which may count up or down any number of steps, each cycle, dependent upon the magnitude as well as the sensed difference between the signal from sensor 6 and voltages $V_1$ and $V_2$ representing the preset preferred range.

Figure 6:
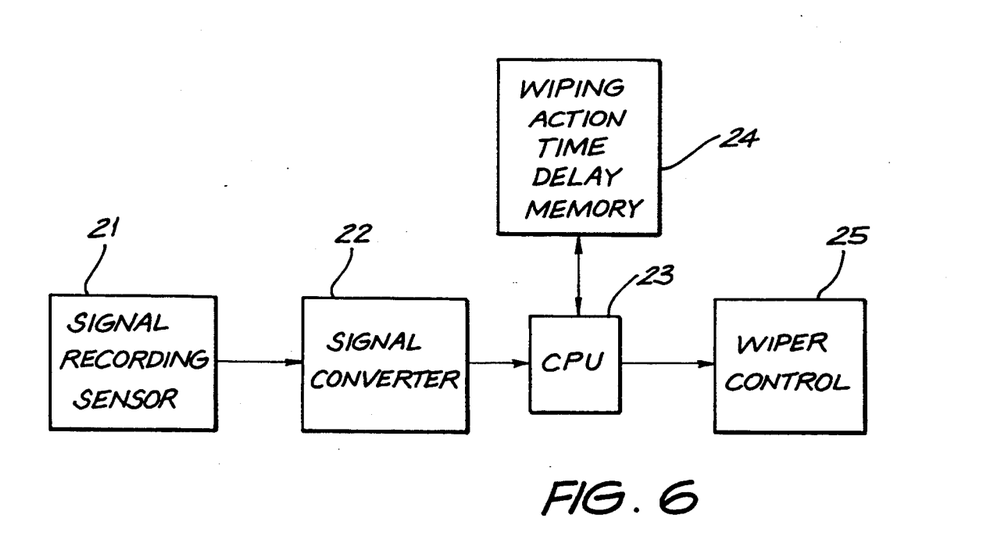
FIG. 6 is a basic block diagram showing the operating function of a second embodiment of a control system for the invention.

FIG. 6 illustrates the logical steps of a programmed microprocessor which, in another embodiment of the invention, constitutes the automatic wiper control 7 shown in FIG. 1. The sensor 21 records the signal from moisture sensor 6 of the water volume displaced by or the size of the water wall or wave being swept in front of, the wiper blade 2 as it crosses the windscreen 1 for every wiping cycle. The signal from moisture sensor 6 provided to the sensor 21 is continuously monitored and its maximum level for each wiping cycle recorded in a register and the minimum level recorded in another register. The minimum level will generally correspond to the substantially dry screen immediately after the blade 2 has passed the moisture sensor 6. The difference of the two registers is calculated every wiping cycle and outputed from the signal converter 22. This operation makes allowances for variations due to component tolerances or heat etc. That signal is received by the central processor 23 which also receives a signal 24 stored in memory defining the last used ("current") wiping action time delay. Thus the wiping action time delay signal 24 is an inverse function of the true rate of wiping the windscreen.

By combining the information of signals 22 and 24 the central processor 23 can determine what the wiper delay should be to bring the signal level 22 back to a predetermined optimum value.

Figure 7:
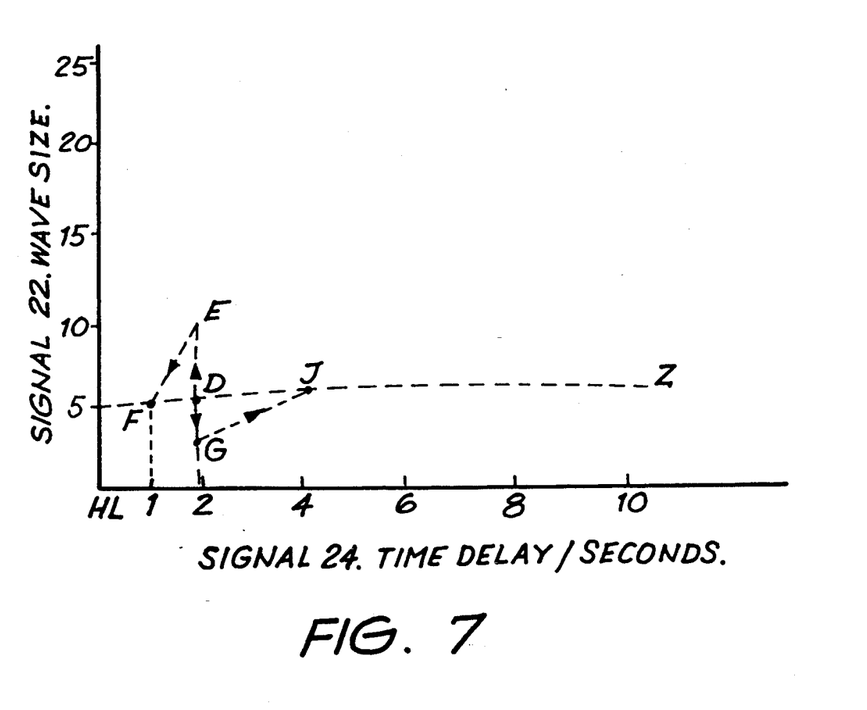
FIG. 7 is a graph illustrating the basis for determining regulation of wiping rates in accordance with predetermined optimum wiping rates for given precipitation levels.

In FIG. 7, as seen in conjunction with FIG. 6, input 24 into the processor 23 corresponds to the wiper time delay since the last wiping action, nominally indicated in seconds of delay between wiping actions and where H and L represent high and low speed continuous modes of operation. A second input, input 22, into the processor 23 relates to the wave size, or the amount of water swept by the wiper blade 2 during the last wiping action and is nominally represented on a scale 0-25, the signal being generally proportional to the quantity of water.

The processor 23 is programmed to seek to set a new wiper delay 24, to bring the wave size 22 back to an optimum predetermined value Z. In FIG. 7, the optimum wave size Z has a nominal value of 5. At point D the wiper delay 24 is 2 seconds. If the rain intensity doubles and therefore the wave size 22 on the next wiping action increases to point E with a nominal value 10, the processor 23 determines that the wave size 22 can be returned to its optimum value Z at point F if the wiper delay 24 is reduced to 1 second, hence doubling the wiping rate. Likewise with a reduction in wave size 22 from point D to point G would cause the processor 23 to adjust the wiper delay 24 from 2 seconds to 4 seconds bringing the wave size 22 from point G to point J.

These adjustments by the processor 23 are carried out prior to the next wiping cycle and fed to the wiper controller 25 to implement the action by controlling motor controller 4. The stored wiping action time delay 24 is checked and adjusted every wiping cycle to maintain where possible the preselected optimum wave size Z. These adjustments also include continuous low and high speed wiping rates, L and H respectively.

The processor 23 and controller 25 can be constructed and programmed in various ways in order to produced the described operating characteristics. For instance the devices may be microprocessors including "maps" to be looked up in accordance with the wave size and wiper rate inputs, the mapping locations providing the pre-programmed appropriate outputs. Alternatively the devices could be mathematically programmed to carry out predetermined algorithms in deriving the required outputs.

What is claimed is:

1. A windscreen wiping system having a wiper motor for driving a windscreen wiper blade, moisture sensor means for measuring a quantitative value of moisture on the windscreen during a current wiper action, and automatic wiper control means for setting a future wiping rate of said wiper blade dependent on present wiping rate and said quantitative measure of moisture, wherein said automatic wiper control means comprises:

input means for receiving a moisture signal from said moisture sensor means having a value corresponding to said quantitative value of moisture;

processing means for determining a control signal by applying a current wiping rate value and said moisture signal value to preprogrammed data, said preprogrammed data setting a control signal value, indexed by current wiping rate and moisture measure, determined to be appropriate for a current absolute moisture accumulation rate; and output means for providing said control signal to said wiper motor to set a new wiper rate.

2. A windscreen wiping system as recited in claim 1, wherein said moisture sensor means measures a quantitative value indicative of the size of a water wave preceding the wiper blade as it wipes moisture from the screen.

3. A windscreen wiping system as recited in claim 2, wherein said automatic wiper control processing means further includes means for retaining current wiping rate information for use in setting said control signal, means for comparing said moisture signal value to a predetermined range of values and determining a relative moisture value as being one of a positive value, a negative value and a zero value, and means for defining the control signal so as to set a future wiping rate to be, respectively, greater than, less than, or equal to the current wiping rate retained in the retaining means, depending on said determined relative moisture value.

4. A windscreen wiping system as recited in claim 3, wherein the means for retaining current wiping rate information and means for defining the control signal are an up/down counter means and an associated decoder means.

5. A windscreen wiping system as recited in claim 3, wherein said means for comparing said moisture signal value to a predetermined range of values includes means for determining a quantity indicating a magnitude of discrepancy between a current wiping rate and a rate based upon said moisture signal value, and the control signal is set to provide a future wiping rate varying from the current wiping rate in proportion to the magnitude of such discrepancy.

6. A method of controlling a vehicle windscreen wiper comprising the steps of:

directing radiant energy from the vehicle interior to a detection region of the windscreen, swept by the windscreen wiper, at a preselected angle such that the directed radiant energy will be substantially totally internally reflected by the windscreen only when the exterior surface is dry;

detecting the radiant energy reflected by the windscreen and determining the amount of the reflected radiant energy;

electronically processing the determined amount of reflected radiant energy that is detected during at least one portion of each action of the windscreen wiper including the radiant energy reflected by a wall of water in advance of the wiper as the wiper passes said detection region to set an output; and controlling speed of motion of the windscreen wiper, or a time delay from one action of the windscreen wiper to the next action of the wiper, according to said output based on the processing of the amount of reflected radiant energy detected during a previous action of the windscreen wiper.

7. The method as defined in claim 6 wherein the radiant energy is light energy.

8. The method as defined in claim 7 wherein the amount of reflected light energy is determined substantially only at the time the wiper blade passes the detection region at which the light is directed at the windscreen.

9. The method as defined in claim 7 wherein the light energy is directed as a plurality of parallel light beams.

10. The method as defined in claim 7 wherein the light energy is infra-red light.

11. A device for controlling a vehicle windscreen wiper comprising:
- a radiant energy source for directing radiant energy onto a surface of the windscreen, at a detection region to be swept by the windscreen wiper, from the vehicle interior;
- a radiant energy detector for detecting the directed radiant energy reflected by said windscreen surface and for producing a signal corresponding to the detected amount of reflected radiant energy; and
- a processor for setting an output which determines speed of a windscreen wiper action, or a time delay between a windscreen wiper action and the next windscreen wiper action, substantially based upon the detected amount of reflected light from a wall of water in advance of the wiper as the wiper passes said detection region during a previous windscreen wiper action.

12. The device of claim 11 wherein the radiant energy source is a light source and the radiant energy detector is a light detector.

13. The device as defined in claim 12 wherein the light source produces at least one beam of directed light, and said light source and light detector are housed in a single unit.

14. The device as defined in claim 13 wherein the light source is a plurality of infra-red LEDs producing a plurality of spaced apart parallel beams and the light detector is a corresponding number of infra-red detectors.

15. The device as defined in claim 12 further comprising a prismatic lens having mutually opposite front and rear faces, mutually opposite side faces therebetween, a plurality of infra-red LEDs in the rear face proximate one side face defining the light source, a corresponding plurality of detecting diodes in the rear face proximate the other side face defining the light detector, and internal reflective surfaces in each side face proximate the front face and lying in the path of the light beam.

16. A vehicle windscreen wiper control assembly comprising:
- a windscreen wiper
- a light source mounted relative to a vehicle windscreen for directing light from the vehicle interior at an outside region of the windscreen surface swept by the windscreen wiper, at an angle so that said directed light is substantially totally internally reflected by the outside surface of the windscreen only when the windscreen surface is dry;
- a light detector mounted relative to the light source and the windscreen so as to detect light from the source reflected by the outside windscreen surface and providing a signal dependant on the amount of detected reflected light; and
- an electronic processor device connected to the light detector and producing a signal for setting speed of a windscreen wiper action or a time delay between a windscreen wiper action and the next windscreen wiper action substantially dependant upon the amount of reflected light detected as a result of a wall of water in advance of the wiper as the wiper passes said region during a previous wiping action.

17. The assembly as defined in claim 16 wherein the light source, light detector and processor device are housed in a single rigid unit mounted on the interior of the windscreen, and the light source produces a plurality of parallel beams.

18. The assembly as defined in claim 16 further comprising a prismatic lens having mutually opposite front and rear faces, mutually opposite side faces therebetween, a plurality of infra-red LEDs in the rear face proximate one side face defining the light source, a corresponding plurality of detecting diodes in the rear face proximate the other side face defining the light detector, and internal reflective surfaces in each side face proximate the front face and lying in the path of the light beam.

19. A windscreen wiper control comprising:
- a device for determining moisture quantity collected by a wiper blade from a windscreen during each wiper action as the wiper blade passes a detection region on the windscreen by detecting variation of radiant energy at said detection region as a result of a wall of water in advance of the wiper blade as it passes said region;
- electronic logic circuit means for receiving and processing signals from the device to compare moisture quantity signals proportional to the magnitude of the wall of water for respective wiper actions; and
- means for controlling speed or frequency of each wiper action dependent upon the signals received during a previous wiper action.

20. A method for controlling a vehicle windscreen wiper comprising the steps of:
- directing radiant energy from the vehicle interior to a region of the windscreen, swept by the windscreen wiper, at a preselected angle such that the directed radiant energy will be substantially totally internally reflected by the windscreen only when the exterior surface is dry;
- detecting the radiant energy reflected by the windscreen and determining the amount of the reflected radiant energy reflected by a wall of water in advance of the wiper as the wiper passes said region to set an output value; and
- controlling speed of motion of the windscreen wiper, or a time delay from one action of the windscreen wiper to the next action of the wiper, in accordance with said output value.

21. A device for controlling a vehicle windscreen wiper comprising:
- a radiant energy source for directing radiant energy onto a surface of the windscreen, at a point or region to be swept by the windscreen wiper, from the vehicle interior;
- a radiant energy detector for detecting the directed radiant energy when reflected by a windscreen surface and for producing a signal, corresponding to the detected amount of reflected radiant energy from a wall of water in advance of the wiper as the wiper passes said point or region, to set an output value; and
- means for controlling speed of motion of the windscreen wiper, or time delay from one action of the windscreen wiper to the next action of the wiper, in accordance with said output value.

22. A device for controlling a vehicle windscreen wiper comprising:
- windscreen wiper means including a wiper blade for sweeping moisture from an area of a windscreen so as to form a wall of water in advance of said wiper blade;

detector means including a radiant energy source for directing radiant energy at a detection area of said windscreen and a radiant energy detector for detecting radiant energy reflected therefrom, said detector producing a signal of magnitude that varies in accordance with loss of energy by diffusion through said wall of water;

electronic logic circuit means for processing said detector signal to produce an output signal which is directly related to the loss of energy as a measure of the amount of moisture wiped by the wiper blade at said detection area during a sweep of said blade on said windowscreen; and wiper control processing means for processing said logic circuit means output signal and operating to control the next sweep of said wiper blade in a manner depending on the amount of moisture detected at said detection area.

23. A method for controlling a vehicle windscreen wiper comprising the steps of:

detecting the presence of moisture on a windscreen by measuring variation of radiant energy reflected from a surface of the windscreen;

initiating a first wiping action of a windscreen wiper blade in response to said detection of moisture so as to produce a wall of water in advance of said blade;

electronically processing a detection signal resulting from detection of moisture in said wall of water in advance of the wiper blade to provide a signal indicating an amount of such moisture; and controlling speed of sweep of a next sweep of the wiper blade according to said signal indicating amount of moisture.

24. A method for controlling a vehicle windscreen wiper comprising the steps of:

detecting the presence of moisture on a windscreen by measuring variation of radiant energy detected on a windscreen surface;

initiating a first wiping action of a windscreen wiper blade in response to said detection of moisture so as to produce a wall of water in advance of said blade;

electronically processing a detection signal resulting from detection of moisture in said wall of water in advance of the wiper blade to provide a signal indicating an amount of such moisture; and controlling a lag time between said sweep and a next sweep of said wiper blade in accordance with said signal indicating amount of moisture.

* * * * *